United States Patent [19]
Wilhelm

[11] Patent Number: 6,026,813
[45] Date of Patent: Feb. 22, 2000

[54] MALE URINARY INCONTINENCE DEVICE

[76] Inventor: John R. Wilhelm, 11605 Split Rail Ct., Rockville, Md. 20852

[21] Appl. No.: 09/292,001

[22] Filed: Apr. 15, 1999

Related U.S. Application Data

[60] Provisional application No. 60/082,560, Apr. 21, 1998.

[51] Int. Cl.[7] .................................................. A61F 5/48
[52] U.S. Cl. ................................. 128/885; 128/DIG. 25
[58] Field of Search ................................... 128/869, 885, 128/886, DIG. 25; 600/29–31

[56] References Cited

U.S. PATENT DOCUMENTS

| | | | |
|---|---|---|---|
| 2,756,753 | 7/1956 | Means | 128/885 |
| 3,147,754 | 9/1964 | Koessler | 128/885 |
| 4,834,115 | 5/1989 | Stewart | 128/885 |
| 5,415,179 | 5/1995 | Mendoza | 128/DIG. 25 |
| 5,439,007 | 8/1995 | Fischer | 128/DIG. 25 |

*Primary Examiner*—Michael A. Brown
*Attorney, Agent, or Firm*—Vorys, Sater, Seymour and Pease LLP

[57] ABSTRACT

A male urinary incontinence device includes a U-shaped body member supporting a bar extending across the ends of the body member. The bar, which is pivotally connected to one end of the body member and releasably latched to the opposite end, supports a shaft for reciprocative movement relative to a curved compression reaction portion of the body member. A pad on an end of the shaft is shaped to compress a penis between the pad and the compression reaction portion with sufficient pressure to stop flow of urine, but without discomfort. The shaft is advanced toward the compression reaction portion by pressing on a free end of the shaft and is held in position by engagement of a pawl with a rachet on the shaft. The shaft, which is prevented from rotation, is released to fall away from the compression reaction portion of the body member by withdrawing the pawl from the rachet.

8 Claims, 1 Drawing Sheet

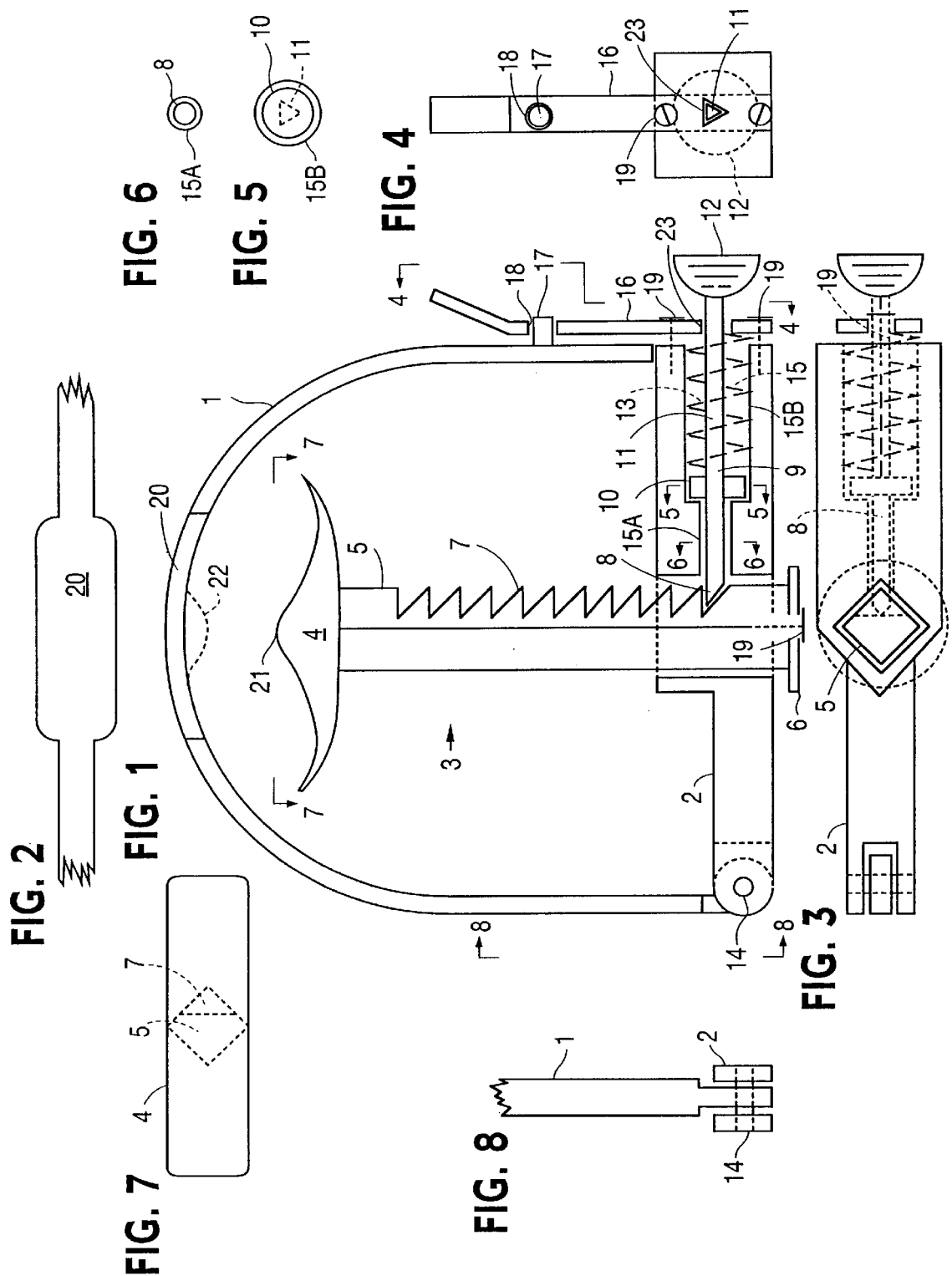

MALE URINARY INCONTINENCE DEVICE

CROSS REFERENCE TO PRIOR APPLICATION

This application claims the benefit of provisional application No. 60/082,560 filed Apr. 21, 1998, incorporated herein by reference.

BACKGROUND OF THE INVENTION

This invention is concerned with male urinary incontinence devices, and is more particularly concerned with a male urinary incontinence device that improves upon the device disclosed in U.S. Pat. No. 5,415,179 granted May 16, 1995, incorporated herein by reference.

As described in the patent, a device for controlling male urinary incontinence comprises a U-shaped lower body member, an upper bar, and compression means located on the bar. The lower body member, circular in cross-section, acts, in effect, as one support for a clamping force. The bar is hingedly connected at one end to one end of the body member and is releasably locked to the other end of the body member. The compression means comprises a screw shaft which passes through a hole in the bar. The bar has a head on an end of the shaft above the bar, engageable by the fingers of a user, and a conical foot on the opposite end of the shaft.

In the use of the device of the patent, the bar is unlocked from the body member, so that the free end of the bar is located away from the body member. A penis is then placed within the cradle of the U-shaped body, and the bar is rotated back toward the body member and locked in place. The position of the shaft is then selected by turning the head of the shaft until the conical foot contacts the penis and provides sufficient pressure against the lower body member to stop urine flow.

The device of the patent has a number of disadvantages. First, to release its grip upon the penis when urination is desired, the bar must be unlocked and rotated away from the body member. Second, because of the conical shape of the foot, the area of contact of the foot with the urethra is limited, so that providing sufficient restriction of urine flow requires uncomfortable pressure of the foot on the penis. Third, the body member is bulky and imparts bulkiness to the whole device.

BRIEF DESCRIPTION OF THE INVENTION

The present invention provides an improved male urinary incontinence device that overcomes the disadvantages of the device of the aforesaid patent. In the device of the invention, the configuration of the body member is such that bulkiness of the body member is significantly reduced, and the penis-receiving opening of the body member is significantly enlarged, so that the penis can be easily inserted and withdrawn, even without moving the bar. A racheted shaft replaces the screw shaft of the patent, and the penis-engaging end of the shaft is shaped to apply sufficient pressure to a substantial length of the urethra without causing discomfort. Furthermore, pressure on the penis is achieved simply by pressing on an end of the shaft, and release of pressure on the penis is achieved simply by withdrawing a pawl from the rachet on the shaft.

BRIEF DESCRIPTION OF THE DRAWINGS

The invention will be further described in conjunction with the accompanying drawings, which illustrate a preferred (best mode) embodiment, and wherein:

FIG. 1 is a vertical sectional view of a device of the invention;

FIG. 2 is a fragmentary plan view showing the configuration of the top of the device;

FIG. 3 is a bottom plan view;

FIG. 4 is an end elevation view taken along line A—A in FIG. 1;

FIG. 5 is a sectional view taken along line B—B in FIG. 1;

FIG. 6 is a sectional view taken along line C—C in FIG. 1;

FIG. 7 is a top plan view of a penis-engaging pad taken along line D—D in FIG. 1; and FIG. 8 is a fragmentary end elevation view taken along line E—E in FIG. 1.

DETAILED DESCRIPTION OF THE INVENTION

The male urinary incontinence device of the invention comprises a frame having a U-shaped body member 1 and a bar 2 pivotally supported on one end of the body member by a hinge 14 and releasably latched to the opposite end of the body member by a latch. A compression device 3 comprises a shaft 5 supported for reciprocative movement through the bar 2 and having a penis-engaging pad 4 at one end and a finger-engaging foot 6 at an opposite, free end.

The shaft 5 has a rachet 7 with a series of teeth extending along one side of the shaft and engageable with a pawl 8 on an end of a plunger 9 having a shaft 11, the opposite end of the plunger being provided with a finger-engaging portion, such as a knob 12. The pawl 8 moves in a cylindrical bore 15A and is biased into engagement with the rachet by a spring 13 compressed in cylindrical bore 15B of a plunger cavity 15 of the bar 2 between a cylindrical abutment 10 on the rod 11 and a plate 16 overlying one of the legs of the U-shaped body member 1.

The plate 16 is attached to an end of the bar 2 by screws 19 and is resiliently flexible so that finger pressure on a tab at the end of the plate can bend the plate to release a lug 17 on the leg of the body member 1 from an opening 18 in the plate. The end of the bar 2 on which the plate 16 is mounted is thus releasably latched to the body member 1 to permit the bar to be pivoted downwardly relative to the body member.

In the form shown, the shape of the rod 11 and the shape of a hole 23 in the plate 16 are chosen (e.g., triangular) to prevent rotation of the rod 11 about its axis. Similarly, the shape of the shaft 5 and the shape of the bore of the bar 2 in which the shaft 5 reciprocates through the bar are chosen (e.g., square) to prevent axial rotation of the shaft 5. Other shapes, or other mechanisms, such as a pin on the bar 2 riding in a longitudinal groove of the shaft 5, can be used to prevent rotation of the shaft (or, similarly, the rod 11).

The U-shaped body member 1 defines an opening internally of the body member into which a penis can be inserted between a rounded ridge 21 at the center of the pad 4 and a compression reaction portion 20 in the curved part of the U-shaped body member. The rounded ridge 21 is elongated in the direction of urine flow (into the plane of FIG. 1), and an opposing rounded and elongated ridge 22 may be provided on the compression reaction portion 20.

In the preferred form, the body member 1 has a cross-section sufficiently small to minimize the mass of the body member, but yet to provide the desired rigidity of the body member (which can be ensured by choosing an appropriate cross-sectional configuration, e.g., T-shaped). As shown in FIG. 2, the compression reaction portion 20 of the body member, which opposes the thrust of the compression device 3, has sufficient length in the direction of urine flow to ensure a comfortable and effective reaction surface.

In the preferred embodiment, the inside diameter of the curved portion of the body member is approximately 1 inch, and the pad measures about ⅝ of an inch in the direction of urine flow and extends about ⅔ of the way across the width of the body member. The cupped shape of the pad, shown in FIG. 1, is intended to embrace the penis and guide the rounded ridge 21 to the location of the urethra. The tapered extremities of the pad, and the material of which the pad is composed (e.g., an appropriate plastic) are intended to provide flexibility to increase comfort while the penis is compressed between the pad and the compression reaction portion 20. It is desired to apply sufficient pressure to the urethra to prevent the flow of urine without significantly restricting blood flow in the penis.

In the use of the device of the invention, the knob 12 is pulled to release the pawl 8 from the rachet 7 and allow the shaft 5 to fall under the influence of gravity. When the knob 12 is released, the spring 13 moves the pawl 8 to engage the rachet 7. The penis is inserted between the pad 4 and the compression reaction portion 20, and the foot 6 of the shaft 5 is pressed toward the bar 2 to move the pad 4 against the penis and to compress the penis between the pad 4 and the compression reaction portion 20. When urination is desired, the knob 12 is pulled to withdraw the pawl 8 from the rachet 7, allowing the shaft 5 to fall under the influence of gravity to release the penis. If desired, the bar 2 can be pivoted to open the frame, but this is not necessary, and the bar can be fixed to the body member, because when the pad 4 is dropped to a position against the bar 2, a large opening within the frame is provided.

While a preferred embodiment of the invention has been shown and described, it will be apparent to those skilled in the art, that modifications can be made without departing from the principles and spirit of the invention, the scope of which is defined in the appended claims. For example, the frame can be a one-piece plastic annulus with an enlargement having a cavity in which the pawl rod and bias spring are contained. Also, a spring can be added to bias the shaft 5 downwardly.

The invention claimed is:

1. A male urinary incontinence device comprises a frame defining an opening for insertion of a penis, the frame having a penis-engaging portion against which a penis is to be pressed and having a shaft supported on the frame for reciprocative movement toward and away from the penis-engaging-portion, the shaft having a penis-engaging pad on an end of the shaft facing the penis-engaging portion of the frame, whereby pressure can be applied to the urethra of a penis by movement of the shaft toward the penis-engaging portion of the frame, and the shaft having a rachet cooperable with a pawl supported on the frame and spring biased into engagement with the rachet, whereby the position of the pad relative to the penis engaging portion of the frame can be maintained until the pawl is withdrawn from the rachet to permit the pad to move away from the penis-engaging portion of the frame.

2. The device of claim 1, wherein the shaft and the frame have cooperable portions that prevent rotation of the shaft on the frame.

3. The device of claim 1, wherein the shaft has a finger-engageable portion on an end opposite to the pad for moving the pad toward the penis-engaging portion of the frame.

4. The device of claim 1, wherein the pad and the penis-engaging portion of the frame are shaped to provide an elongated area of contact with the penis in the direction of urine flow.

5. The device of claim 1, wherein the pad is shaped to embrace a penis when pressed against the penis.

6. The device of claim 1, wherein the pawl is at an end of a rod reciprocatively supported on the frame and having a finger-engageable member on an end opposite to the pawl to move the pawl away from the rachet against the spring bias.

7. The device of claim 1, wherein the frame has a generally U-shaped body member and a bar extending across ends of the U-shaped body member and supporting the shaft thereon, and wherein the penis-engaging portion of the frame comprises a curved portion of the U-shaped body member.

8. The device of claim 7, wherein the bar is pivotally connected to one end of the U-shaped body member and is releasably latched to the opposite end of the U-shaped body member.

* * * * *

UNITED STATES PATENT AND TRADEMARK OFFICE
CERTIFICATE OF CORRECTION

PATENT NO. : 6,026,813
DATED : February 22, 2000
INVENTOR(S) : John R. WILHELM

It is certified that error appears in the above-identified patent and that said Letters Patent is hereby corrected as shown below:

Column 2, line 6, delete "A--A" and insert --4--4--;
          line 8, delete "B--B" and insert --5--5--;
          line 10, delete "C--C" and insert --6--6--;
          line 13, delete "D--D" and insert --7--7--;
          line 15, delete "E--E" and insert --8--8--.

Signed and Sealed this

Twentieth Day of March, 2001

Attest:

NICHOLAS P. GODICI

*Attesting Officer*    *Acting Director of the United States Patent and Trademark Office*